Figure 1:
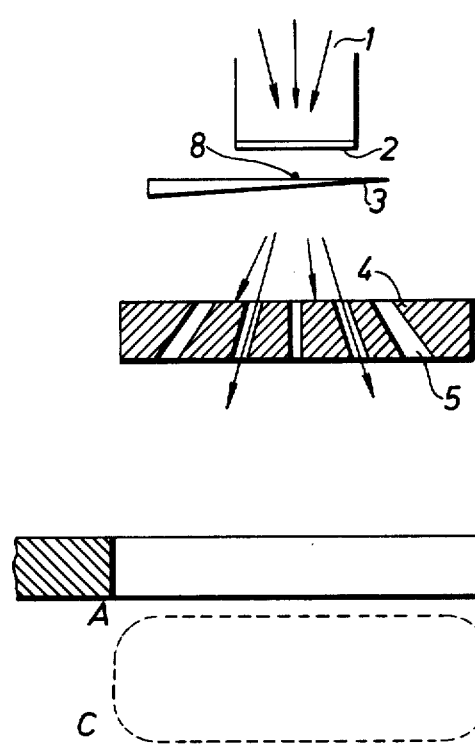

United States Patent
Brahme

[11] 4,020,356
[45] Apr. 26, 1977

[54] ABSORPTION BODY

[75] Inventor: Anders Sven Brahme, Bromma, Sweden

[73] Assignee: Scanditronix, Instrument AB, Uppsala, Sweden

[22] Filed: Apr. 10, 1975

[21] Appl. No.: 567,141

[30] Foreign Application Priority Data
Apr. 10, 1974 Sweden .......................... 7404930

[52] U.S. Cl. ............................... 250/510; 250/504
[51] Int. Cl.² .................................... G21K 3/00
[58] Field of Search .......... 250/505, 510, 511, 504

[56] References Cited
UNITED STATES PATENTS

| | | | |
|---|---|---|---|
| 2,724,059 | 11/1955 | Gale | 250/492 B |
| 3,248,547 | 4/1966 | Geijn | 250/510 |
| 3,665,186 | 5/1972 | Tajima | 250/510 |
| 3,678,233 | 7/1972 | Faw et al. | 250/510 |
| 3,717,768 | 2/1973 | Edhom et al. | 250/510 |

Primary Examiner—Archie R. Borchelt
Assistant Examiner—B. C. Anderson
Attorney, Agent, or Firm—Seidel, Gonda & Goldhammer

[57] ABSTRACT

An absorption body for controlling the energy distribution of radiation passing into a volume being irradiated is disclosed. The absorption body has a pattern of holes which influences the energy distribution of radiation passing through the body. The energy distribution and the spatial distribution of the radiation penetrating the volume being irradiated is thereby controlled both in the depth direction of the volume and transversely thereto.

10 Claims, 8 Drawing Figures

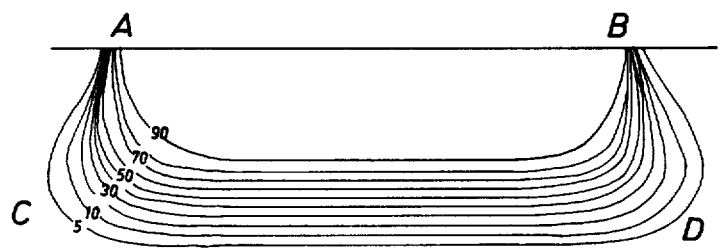
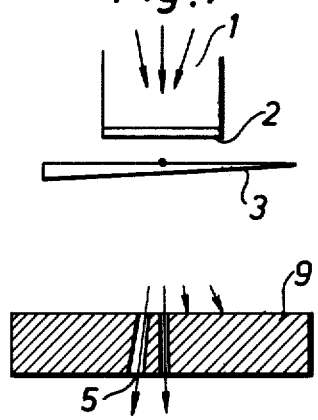
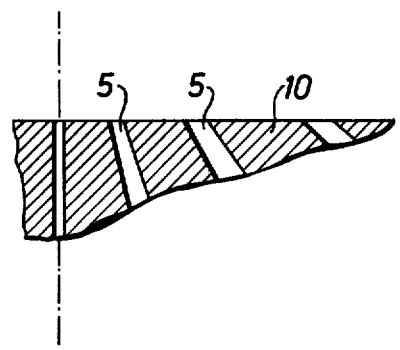
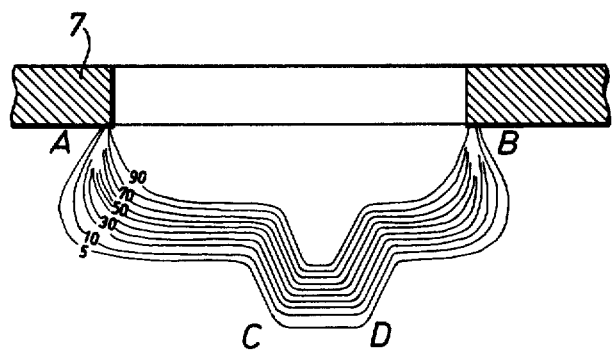

ABSORPTION BODY

The present invention refers to a device adapted during radiation with high energy particles to influence both the spatial and the energetic distribution of the particle radiation over the field exposed to radiation.

High energy particles, in particular electrons, are used for therapeutic purposes. For such purposes the particle radiation has an energy within the range extending from about 1 to about 50 MeV. The depth of penetration of the particle radiation into the tissue, the so-called range, expressed in centimeters, is approximately equal to the energy of the particle radiation, expressed in MeV, divided by 2. When the particle radiation enters into the tissue three basic processes take place namely scattering, energy transfer and production of bremsstrahlung. Scattering means that the entering particles are subjected to elastic impacts without loosing kinetic energy. Energy transfer occurs during collision with shell electrons due to non-elastic impact causing certain shell electrons to be released (secondary electrons) where the primary electron continues to move with reduced energy in a changed direction to push out new electrons in other atoms. The atom which has been deprived of an electron thus becomes a positive ion which means that an ionization takes place. Production of bremsstrahlung occurs when the incoming radiation enters into the range of the atomic nucleus itself and thereby looses energy. The kinetic energy released in this way appears in the form of electromagnetic radiation. The ionization density in the processes described above is the basis of the dose distribution which is a factor of great importance for therapeutic purposes and which is proportional to the energy absorbed per unit mass of the tissue material. The distribution of the absorbed dose is expressed with the aid of so-called dose curves. For electrons the dose is not at its maximum in the surface of the tissue but rather a distance inside the tissue. Normally the maximum extends from ¼ to ½ of the total range of the particle radiation. A clear survey of the dose distribution in the irradiated range is obtained from the so called isodose diagrams.

The basic problem of every therapy is to adapt the dose distribution to the target proper i.e. the tumor to be irradiated. Various mehtods are used for this purpose. It is known to vary the energy of the electrons and thereby to alter the depth of penetration of the particle radiation. The particle radiation from the accelerator normally has substantially circular cross section of some millimeters' diameter. The particle radiation is spread with the aid of stationary spreading foils having a thickness corresponding to the size and energy of the radiation field. The foils may consist of copper, nickel, gold, lead etc. Thus, these foils are intended to increase the diameter of the particle radiation and to improve the homogeneity thereof. It is also known to use additional spreading foils consisting of thin copper plate adapted to the shape of the target area and supported by a plastic foil. It is also known to widen the diameter of the beam with the aid of electro-magnets diverting the beam. The size of the irradiation field may also be varied with the aid of quite a different technique according to which a non-enlarged beam is used which similarly to the electron beam in a television receiver is caused to perform a reciprocatory sweeping movement over the region to be irradiated. According to another similar technique the particle radiation may be caused to oscillate over the irradiated range.

Finally, it is known to limit the irradiated field with the aid of tubes consisting of brass, perspex or the like. All the procedures described above enable both the spatial distribution and the intensity distribution of the particle radiation over the radiated range to be changed. However, it is not possible with the aid of the said processes to influence in an appreciable degree the dose distribution in the depth direction i.e. the dose distribution within the tissue itself.

The present invention is directed to eliminating the above mentioned drawback and at the same time to produce well balanced and homogeneous radiation fields. The characteristic features of the invention appear from the attached claims.

The secondary absorption body according to the invention can be adapted to every imaginable target and it is simple and cheap to manufacture and may be used in every available irradiation apparatus.

Figure 2:
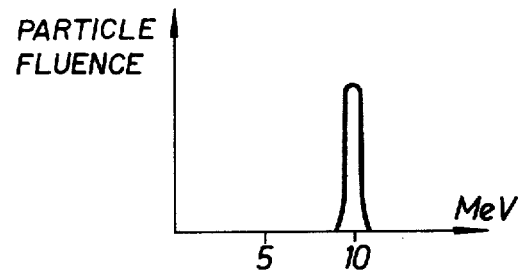
Figure 3:
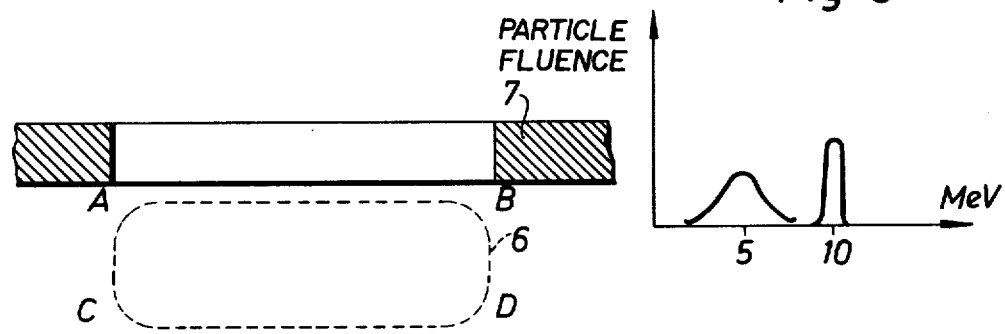
Figure 4:
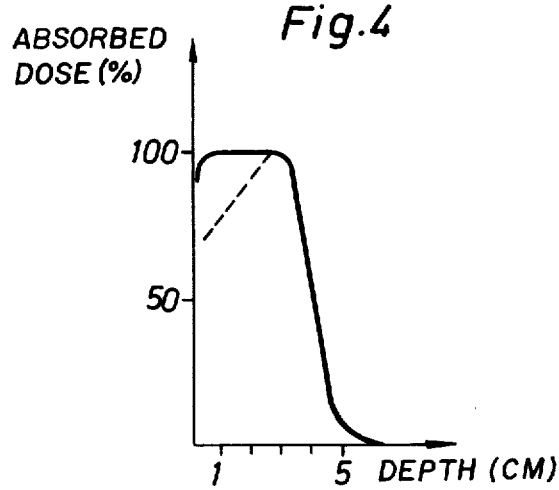
Figure 5:
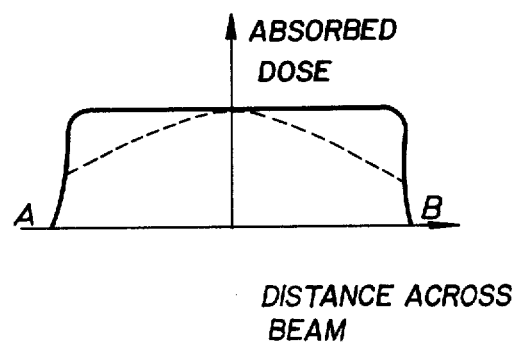

Various embodiments of the invention will be described hereafter by reference to the enclosed drawings in which FIG. 1 shows a device according to the invention, FIGS. 2 and 3 are diagrams showing the energy distribution of the particle radiation in various points in the device according to the invention, FIG. 4 is a diagram showing the dose distribution with and without use of the absorption body according to the invention, FIG. 5 is a diagram showing the dose distribution across the radiation with or without use of the absorption body according to the invention, FIG. 6 is an isodose diagram of the radiation range ABCD in FIG. 1 when the absorption body shown in FIG. 1 is used, FIG. 7 illustrates another embodiment of the invention and FIG. 8 shows another embodiment of the absorption body according to the invention.

High energy electron radiation 1 is diffused, on the one hand, by a vacuum window 2 in a radiation source and, on the other hand, by a primary spreading foil 3 consisting of gold or lead. The thickness of the spreading foil may vary along the length of the foil. The radiation as scattered by the spreading foil meets an absorption body 4 consisting of graphite, plastic, beryllium or any other suitable material. The absorption body 4 is provided with an array of holes 5 through which the particles of the scattered radiation may pass without hindrance. The volume ABCD of the tissue and its target zone 6 to be irradiated is surrounded in a way known in itself by a collimator 7. Delimiting means other than the collimator 7 shown can be used, these means not forming a part of the present invention and accordingly not being described in greater detail here. FIG. 2 shows a diagram of the energy distribution of the particle radiation as spread by the foil 3 and the vacuum window 2. The abscissa indicates the energy of the particle radiation in magaelectron volt (MeV) whereas the ordinate indicates the number of particles having the energy in question. After passage through the absorption body 4 the particle radiation assumes the energy distribution appearing from FIG. 3. Thus, it will be seen that a certain part of the original energy still is left in the radiation behind the absorption body whereas at the same time a certain number of particles have been retarded by the absorption body and the energy thereof has been reduced. The intensity mixing ratio between the energy components may be varied by means of the thickness of foil 3 which for this purpose suitably has a wedge-or similarly shaped cross section. When a suitable intensity mixing ratio has been established it is of course possible to substitute a stationary spreading foil having constant thickness for the spreading foil having varying thickness. It appears from FIG. 4 how the dose is distributed within the tissue, the abscissa indicating the tissue depth in centimeters and the ordinate indicating the dose. The broken line curve shows how the dose is distributed in the depth direction in case the absorption body 4 is not used, whereas the full-line curve shows the dose distribution when the absorption body 4 is used. It appears from FIG. 4 that the dose distribution will be substantially constant and high already after a short depth of penetration.

In the absorption body shown in FIG. 1 the holes 5 are through holes and form patterns of, for example, concentric rings. The diameter of the holes increases with increasing spacing from the central beam. The longitudinal symmetry axes of the holes converge in a crossing point common for all the holes and coinciding with the focussing point 8 of the radiation source. With such a pattern of holes the dose will be distributed across the beam in the way illustrated in the full-line curve in FIG. 5. The broken line curve in FIG. 5 illustrates how the dose would be distributed in the absence of absorption body 4. If the thickness of the absorption body 4 is increased so that the energy component at 5 MeV completely disappears, a dose distribution according to the broken line in FIG. 4 is obtained whereas the dose across the beam will be of the type indicated by full lines in FIG. 5. Thus, it is possible to obtain homogeneous dose distribution across the beam without influencing the depth distribution.

FIG. 6 shows isodose curves in the radiation range ABCD according to FIG. 1 when the absorption body 4 according to FIG. 1 is used. As appears from FIG. 6, the 100 %—isodose substantially covers the whole irradiated tissue volume.

Thus, the absorption body 4 shown in FIG. 1 produces a radiation field which is particularly homogeneous both in the depth- and transverse directions.

FIG. 7 shows an absorption body 9, producing a radiation field having varying depth of penetration. The absorption body 9 here shows a pattern of holes which are grouped around the central beam. The longitudinal symmetry axes of the holes intersect in a common point coinciding with the focussing point 8 of the radiation source. By varying the thickness of the primary spreading foil 3 a desired intersity ratio between high and low energy components in the beam (compare FIG. 3) may be obtained in the tissue field ABCD. The thickness of the spreading foil may, for example, vary from about 0.001 to about 0.003 cm.

In FIG. 8 there is shown an absorption body 10 having a number of through holes 5. The absorption body 10 varying thickness. By providing an absorption body of varying thickness and having a suitable pattern of holes it is thus possible to vary the direction and energy distribution of the incoming radiation in order to obtain a desirable dose distribution both transversely and in the depth direction in the tissue field under radiation (target).

If a non-dispersed electron beam is used for therapeutic purposes and if this beam, by means of magnetic diverting devices or the like is caused to sweep over the radiated range in about the same way as the electron beam in a television receiver, it is possible completely to dispense with the spreading foil. By adapting the diameters of the holes or alternatively the hole density in various zones of the absorption body to the desired dose distribution across the radiation in the tissue and by adapting the thickness of the absorption body to the desired dose distribution in the depth direction within the tissue it is possible to compensate for any deficiencies of the sweeping procedure. If for example the sweep velocity of the beam along a line over the tissue varies sinusoidally, involving low speed in the edge portions of the line and high speed in the central zone of the line, the dose distribution across the beam will be high in the edge ranges of the irradiated zone and low in the central range. However, this distribution can be caused to be constant across the entire irradiated field if the diameters of the holes (alternatively the number of holes) is chosen greater in the central range of the absorption body.

The above described absorption bodies can of course be varied and modified. For example, the holes 5 need not be through holes. Alternatively, the holes 5 may be filled with a material the spreading ability and/or absorption ability of which is lower than in the main portions of the absorption body. It is of course possible to arrange the holes in patterns other than annular patterns, for example hexagonally, square etc. Moreover, the holes need not be circular but may have other shapes. In addition, the holes need not be cylindrical but may have conical shape (in longitudinal section) or other shapes.

The above described embodiments of the invention may be modified and varied in many ways within the frame of the basic idea of the invention.

What we claim is:

1. Device to be used in the irradiation of a limited volume with high-energy particles, characterized by an absorption body having a pattern of holes for simultaneous and controlled influence of both the energy distribution of the radiation and the spatial distribution of the radiation in the depth direction and transversely throughout the radiated volume.

2. Device as claimed in claim 1, characterized in that the absorption body has the shape of a plate of constant thickness, that the holes are substantially evenly distributed over the absorption body and that the symmetry axes of the holes converge towards a point of intersection common to all the symmetry axes and coinciding with the focussing point of the radiation source whereby the dose distribution in the volume in the transverse and depth directions in relation to the direction of radiation is substantially constant in the radiated range.

3. Device as claimed in claim 2, characterized in that the holes are grouped in one or more limited ranges on the plate to vary the dose distribution in the transverse and depth directions of the radiation along said directions.

4. Device as claimed in claim 1, characterized in that the absorption body has a thickness such that the radiation will pass only through the holes themselves whereby the field of radiation will be substantially constant transversely to the radiation.

5. Device as claimed in claim 1, characterized in that the absorption body is made of a material selected from the group consisting of graphite, plastic, beryllium, and any other material having a low Z-value.

6. Device as claimed in claim 1, characterized by a primary spreading foil having constant thickness along its longitudinal direction, said spreading foil preferably being provided adjacent the exit opening of the radiation source to vary the intensity mixing ratio between energy components in the radiation passing to the absorption body.

7. Device as claimed in claim 1, characterized by a primary spreading foil having varying thickness along its longitudinal direction, said spreading foil preferably being provided adjacent the exit opening of the radiation source to vary the intensity mixing ratio between energy components in the radiation passing to the absorption body.

8. Device as claimed in claim 1, characterized in that the holes are through holes and that the diameter of the holes, increases with increasing spacing from the central electron beam.

9. Device as claimed in claim 1, wherein the particle radiation sweeps and/or is electromagnetically spread over the radiated range, characterized in that the holes of the absorption body are provided in a pattern corresponding to the desired dose distribution across the beam and that the absorption body has a thickness corresponding to the desired dose distribution in the depth direction.

10. Device as claimed in claim 9, characterized in that depth of the holes are limited or are at least partially filled with a material having different absorbing and/or spreading properties.

* * * * *